United States Patent [19]

Davis et al.

[11] Patent Number: 5,514,253
[45] Date of Patent: May 7, 1996

[54] METHOD OF MEASURING GAS CONCENTRATIONS AND MICROFABRICATED SENSING DEVICE FOR PRACTICING SAME

[75] Inventors: Graham Davis, Princeton, N.J.; Imants R. Lauks, Rockcliffe Park; Raymond J. Pierce, Ottawa, both of Canada; Cindra A. Widrig, North Wales, Pa.

[73] Assignee: I-Stat Corporation, Princeton, N.J.

[21] Appl. No.: 274,460

[22] Filed: Jul. 13, 1994

[51] Int. Cl.$^6$ ................................................ G01N 27/26
[52] U.S. Cl. .................... 205/782.5; 205/403; 205/431; 205/432; 422/68.1; 422/82.03; 422/82.04
[58] Field of Search ................................ 204/415, 403, 204/431, 432, 153.17, 153.18, 153.16, 421; 422/68.1, 82.03, 82.04

[56] References Cited

U.S. PATENT DOCUMENTS

| | | | |
|---|---|---|---|
| 5,112,455 | 5/1992 | Cozzette et al. | 204/153.17 |
| 5,183,549 | 2/1993 | Joseph et al. | 204/415 |
| 5,246,576 | 9/1993 | Leader et al. | 204/415 |
| 5,346,604 | 9/1994 | Van Sin et al. | 204/415 |
| 5,401,376 | 3/1995 | Foos et al. | 204/415 |

Primary Examiner—Bruce F. Bell
Attorney, Agent, or Firm—Lowe, Price, LeBlanc & Becker

[57] ABSTRACT

A microfabricated sensing device is disclosed, including methods for using the same for the measurement of the concentration of a gas in a sample. Unique sensor configurations are described which substantially eliminate electrode cross-contamination during operation of the microfabricated sensing devices.

38 Claims, 5 Drawing Sheets

METHOD OF MEASURING GAS CONCENTRATIONS AND MICROFABRICATED SENSING DEVICE FOR PRACTICING SAME

FIELD OF THE INVENTION

The present invention relates to methods and devices for measuring the concentration of a gas in a sample, especially a liquid sample. In particular, the present invention relates to a microfabricated sensing device comprising a planar substrate on which is established a configuration of working and counter/reference electrodes such that measurements of the concentration of gas can be performed while minimizing working electrode contamination by components of the counter/reference electrode. Most aptly, the present invention is useful in taking measurements of the concentration of blood gases, including oxygen and carbon dioxide.

BACKGROUND OF THE INVENTION

The measurement of gas concentrations, particularly in blood, is the object of continuing development in the gas analysis field.

The classical Clark electrode technology (*Trans. Am. Soc. Artificial Internal Organs* (1956) 2:41), which has been applied to oxygen measurement in commercially available blood gas analyzers (see, for example, Weinberg U.S. Pat. No. 4,361,540 and Enzer U.S. Pat. No. 4,871,439), does not use planar microfabrication techniques. The gold working electrode is usually made from a drawn wire, having a diameter of about 10 microns, embedded in glass. The small diameter of the electrode reduces effects of sample flow on the sensor output. It should be emphasized, however, that although this electrode is a "microelectrode," it is not made with planar microfabrication methods. In particular, a gas permeable membrane is stretched over the end of the electrode and secured by an O-ring to enclose and isolate the sensor from the sample solution.

It is also well known that classical (i.e., non-microfabricated) Clark oxygen electrodes exhibit silver contamination of the gold electrode surface during normal use. This contamination arises from silver deposition at the gold cathode. Silver contamination of the gold electrode is problematic for two reasons: (i) it affects the oxygen reduction wave as silver and gold have different catalytic activities, and (ii) halothanes and other common anaesthetic gases exhibit significantly greater electrochemical reduction on silver as compared to gold (see, for example, Hall et al. *J. Biomed. Eng.* (1988) 10:319), thus, giving rise to a variable interference current.

With standard Clark electrode technology, the basic approach to obviate this problem has been to position the silver-silver chloride electrode within the electrode barrel several centimeters away from the gold electrode. Even so, during use the membrane must occasionally be removed from the electrode and any silver contamination of the gold surface removed by polishing. This approach is clearly impractical for planar microfabricated sensors where the membrane is manufactured as an integral part of the device.

Considering the prior efforts to manufacture planar oxygen sensors, two aspects are noteworthy: first, the reference electrode and the working electrode are generally positioned in close proximity; second, the electrodes are electrically isolated from the sample by a gas permeable membrane that encloses the electrodes.

For example, U.S. Pat. No. 4,062,750 (Butler) describes an alleged microfabrication method for manufacture of a thin-film polarographic oxygen sensor. This reference describes an array of cathodes on a silicon substrate. In the primary embodiment of this reference, (i) the separation between cathodes and anode in only 25 microns (column 4, line 10) and (ii) the silicon device is assembled into a cylindrical element which enables a gas permeable membrane to be secured over the silicon device by means of an O-ring. Thus, the primary embodiment is essentially a hybrid device in which planar microfabrication is used to manufacture the electrodes, while the electrolyte layer and gas permeable membrane are provided in the same manner as the classical Clark electrode. A second embodiment, discussed at column 16 of this reference, allows the establishment of a gas permeable layer via plasma polymerization. Nonetheless, all the oxygen sensing devices described in this reference position the anode and cathode (or array thereof) in close proximity to each other and enclose both electrodes under a gas permeable membrane.

U.S. Pat. No. 4,534,356 (Papadakis) discloses a planar manufacturing method for the fabrication of a solid state transcutaneous blood gas sensor that utilizes an electrode pair. A gas permeable membrane is used to enclose the structure. Here, a material is applied onto the device which dries to leave a membrane that adheres without requiring an O-ring. The patent asserts that the blood oxygen sensor of the alleged invention needs no pool of electrolyte and that the gas permeable membrane need not be changed, thus, avoiding the need for recalibration. The disclosure provides no teaching regarding electrode configuration and placement, beyond showing that the electrodes are positioned next to each other and that both are enclosed by the gas permeable membrane.

European Patent Application No. 0496521 A1 (Tsukuda) discloses a planar laminated structure for blood oxygen measurement which is alleged to provide the desired longer operational lifetime. In the Tsukuda devices, an enlarged electrolyte reservoir 12 is defined by the layered laminated pieces. This enlarged electrolyte reservoir is in contact with the working electrode 84 and reference electrodes 13. (See, FIG. 5.) The specification explains that the electrodes are located in different layers to allow flexibility in the dimensions of the electrodes and which achieve good sensor lifetime. (See, column 4, lines 28–31.) In other words, the reference electrode must be large enough to be consistent with the desired longer operational lifetime. (See, column 4, lines 1–4.) Likewise, the electrolyte capacity is adjusted to select an appropriate lifetime. (See, column 2, lines 41–57.) However, this reference makes no mention of silver contamination of gold. Furthermore, both the working and reference electrodes are enclosed under the gas permeable membrane 7.

U.S. Pat. No. 4,682,602 (Prohaska) teaches a microfabricated sensor design that can allegedly be used for many analytes. A chamber 3, containing an electrode or transducer, is created with an aperture in the chamber wall. (See, for example, FIG. 1.) The aperture ensures that the electrode is not electrically isolated from the sample. However, it is clear that the intention is to create a substantially enclosed structure, as is readily apparent from an examination of FIGS. 1–3 of this reference. At column 3, lines 52–59, the specification states that two electrodes or transducers can be utilized to form an electrochemical cell within the confines of the enclosed chamber. Essentially, this reference describes a microfabricated version of a pin-hole electrode that is well known in the electrochemical sensor art.

U.S. Pat. No. 4,933,048 (Lauks) describes a reference electrode/working electrode configuration in which the working electrode 10 is completely enclosed by an overlayer 13 that is a membrane or series of membranes that render the working electrode specific to a species to be measured. (See, FIG. 2.) Thus, the working electrode is effectively insulated from the reference electrode. This patent also discloses a reference electrode that wets up rapidly from a dry-stored state and comprises a low impedance path to an external solution. The disclosure of this reference is incorporated in its entirety by reference herein.

U.S. Pat. No. 5,096,669 (Lauks) discloses a disposable device, including a housing, sensor, sample retaining means, and sample conduit. The housing also bears a sensor region in which at least one sensor is located. The disclosure of this reference is incorporated in its entirety by reference herein.

Both open and enclosed oxygen sensor structures are disclosed in U.S. Pat. No. 5,200,051 (Cozzette). (See, for example, columns 41-3 and FIGS. 7A and 7B, respectively.) However, the gold and silver/silver chloride electrodes are positioned in close proximity under the same "open" structured gas permeable membrane. The specification does not suggest the problem of gold electrode contamination by the components of the silver/silver chloride reference electrode and, hence, offers no solution for same. Indeed, FIG. 7A illustrates a sensor configuration in which the gold working electrode is flanked by the silver/silver chloride reference electrode. The disclosure of this reference is incorporated in its entirety by reference herein.

SUMMARY OF THE INVENTION

According to the present invention, a microfabricated sensing device is provided for measuring the concentration of a gas in a liquid sample which device may be operated free of the electrode contamination problem that has plagued previous devices. Thus, a microfabricated sensing device is disclosed which comprises: (a) a working electrode (WE) and a counter/reference electrode (CRE) established on the same planar substrate being separated by a distance effective to minimize WE contamination by components of the CRE; (b) an electrolyte layer (EL) established on the substrate and enclosing the WE; and (c) a gas permeable membrane (GPM) established on but not enclosing the EL and positioned over the WE, each of the GPM and EL having dimensions and configuration relative to the WE such that the flux of gas to the WE, from a liquid sample in contact with the device, is substantially a function of the amount of gas passing through the GPM and not from the open perimeter of the overlaid structures. This embodiment of the present invention is particularly well suited for measurements taken in a liquid sample, including biological fluids, such as blood, in which a component of the liquid (e.g., the aqueous or conductive portion of blood) can provide a low impedance path between the WE and the CRE. In a separate embodiment, the WE and CRE are located on different substrates.

In another embodiment of the present invention, a sensing device is provided which is particularly well suited for measurements taken in a gaseous sample, especially a "wet" gas, i.e., a gas having a high water content or humidity. In this instance, a built-in electrical connection between the WE and the CRE can be provided effectively. Hence, in a preferred embodiment, a microfabricated sensing device is disclosed comprising: (a) a planar substrate; (b) a working electrode (WE) and a counter/reference electrode (CRE) established on the substrate and separated by a horizontal distance effective to minimize WE contamination by components of the CRE; (c) an electrolyte layer (EL) established on the substrate and enclosing the WE; (d) a conducting layer (CL) established on the substrate to provide electrical contact between the WE and the CRE; and (e) a gas permeable membrane (GPM) established on but not enclosing the EL and positioned over the WE, each of the GPM and EL having dimensions and configuration relative to the WE such that the flux of gas to the WE, from a fluid sample in contact with the device, is a function of the amount of gas passing through the GPM. In another embodiment, the EL, which is in electrical contact with the CRE, serves as the CL.

It is also another object of the present invention to provide a method of measuring the concentration of a gas in a liquid sample. For example, in an oxygen measuring embodiment employing amperometric methods, the present invention comprises: (a) providing a microfabricated sensing device, such as that described above; (b) contacting a liquid sample containing a dissolved gas to the device such that the liquid sample provides a low impedance path between the WE and CRE; (c) applying a potential to the WE with respect to the CRE effective to allow molecules of the gas to undergo a redox reaction at the WE; (d) measuring the current output of the device; (e) determining the concentration of the gas.

In another oxygen measuring embodiment, the present method comprises: (a) providing a microfabricated sensing device having a CL establishing electrical contact between the WE and the CRE; (b) contacting a fluid sample containing a gas to the device; (c) applying a potential to the WE with respect to the CRE effective to allow molecules of the gas to undergo a redox reaction at the WE; (d) measuring the current output of the device; and (e) determining the concentration of the gas. As mentioned previously, this latter embodiment is particularly well-suited to a fluid sample comprising a wet gas.

In another embodiment for measuring carbon dioxide using potentiometric methods, the present invention comprises: (a) providing a microfabricated sensing device, such as that described above; (b) contacting a liquid sample containing carbon dioxide gas to the device such that the liquid sample provides a low impedance path between WE and the reference electrode; (c) measuring the potential difference between WE and the reference electrode; and (d) relating the measured potential to the concentration of the gas.

Still another object of the invention relates to the measurement of the concentration of an analyte (such as a gas) in a liquid sample by providing a microfabricated sensing device comprising: (a) a working electrode (WE) and a counter/reference electrode (CRE) established on the same planar substrate, the WE and CRE being substantially different in at least one dimension (such as thickness, width or depth); (b) at least a first layer established over the WE, the WE and CRE being separated by a distance effective to minimize the adverse effects of the substantially different dimension on the topological features of the first layer.

In a specific embodiment, such a device may further comprise a second layer (e.g., a conductive layer) established over the first layer (e.g., an electrolyte layer). Preferably, the second layer is positioned over the WE but does not enclose the first layer. Although the distance separating the electrodes may vary according to each embodiment, the distance is preferably at least about 1 mm.

Other objects of the present invention will be apparent to one of ordinary skill in the art, especially after consideration of the following detailed description of the preferred embodiments. In particular, it should be apparent that other gases that can undergo a redox reaction (e.g., nitrous oxide, carbon monoxide, hydrogen sulfide, and the like) can be measured using the amperometric methods disclosed herein. Also, any gas that can generate a change in pH upon dissolution in water (e.g., sulfur dioxide, nitric oxide, nitrogen dioxide, and the like) can be determined through the potentiometric techniques described in the present application. Other objects that should be apparent to those of ordinary skill in the art include, but are not limited to, processes of making the microfabricated sensing devices of the present invention and other methods of use relating to same.

BRIEF DESCRIPTION OF THE DRAWINGS

As an alternative configuration of an "open" perimeter structure.

DETAILED DESCRIPTION OF THE PREFERRED EMBODIMENTS

In the hands of the present applicants, it was observed that a silver reference electrode, established by a microfabrication process in close proximity to a gold electrode, causes the contamination of the gold surface of the working electrode when the device is operated in an enclosed structure. For example see the structure shown in FIG. 7B of U.S. Pat. No. 5,200,051. While the specific dimensions may vary according to the particular microfabricated device configuration, including the dimensions of the working and counter/reference electrodes, themselves, "close proximity" means that the subject microfabricated electrodes are positioned, generally, within about 1 mm of each other in an enclosed structure. The term "counter/reference," as used in the present invention, is meant to describe an electrode that can serve as a counter electrode, a reference electrode or both.

As will be described further in the discussions to follow, it has been found that electrode contamination, particularly acute in the small distances involved in microfabricated devices, can be overcome effectively by combining aspects of electrode configuration, including the spacing between electrodes, and overlayer design, including the incorporation of a degree of "openness" to the structure. The latter concept, it should be noted, is contrary to the general teaching in the art. Quite surprisingly, the applicants have been able to maintain those advantages that have been the hallmark of the microfabricated devices pioneered by the applicants, as described, for example in U.S. Pat. No. 5,200,051 (Cozzette), including the ability to maintain close control over the dimensions and thicknesses of the components of the microfabricated sensor. Such overall dimensional control, in turn, allows control over sensor response and "wet-up" behavior necessary for establishing predictable sensor characteristics that are utilized advantageously in the disclosed "real time" or "point of care" fluid component analyses. For additional information on the utilization of microfabricated sensors during wet-up, the reader is referred to the disclosure of U.S. Pat. No. 5,112,455 (Cozzette), which is incorporated in its entirety by reference herein.

As mentioned above, electrode contamination is a significant problem, particularly in blood gas measurements that require a certain applied working electrode potential relative to the counter/reference electrode. It should be noted that the present disclosure utilizes a combination counter/reference electrode. However, as would be apparent to those of ordinary skill, separate counter and reference electrodes may also be used. Separate electrodes may require additional processing steps and affect space considerations that are minimized in the combination electrode, however.

Figure 1:
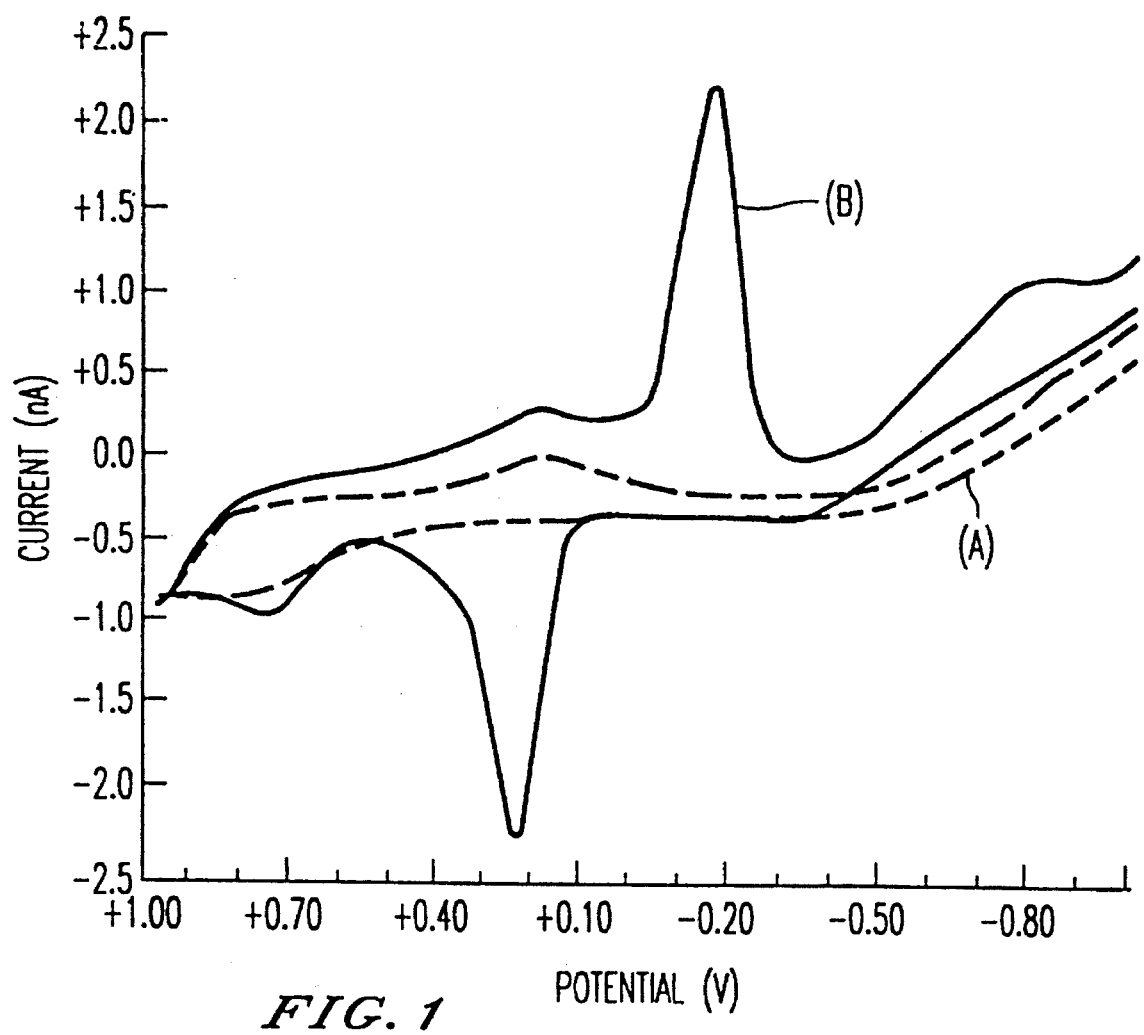
FIG. 1 shows voltammograms for oxygen reduction at gold in the absence (solid line, A) and presence (dashed line, B) of silver contamination.

FIG. 1 shows voltammograms for oxygen reduction at gold in the absence (curve A) and presence (curve B) of silver contamination. Two standard analytical techniques were used to confirm the nature of the contamination: (i) Auger spectroscopy, to identify specifically the presence of silver on the gold surface, and (ii) electrochemical stripping analysis, to quantify the degree of silver contamination.

An "electrolyte layer" is any hydratable material that can accommodate ions and small molecules in a protic environment. In a preferred embodiment of the present invention the electrolyte layer is comprised of photoformable proteinaceous materials, film forming latexes and the like as disclosed in U.S. Pat. No. 5,200,051.

In an enclosed structure, any silver ions lost from the anode are confined to the electrolyte layer. With previously known enclosed microfabricated structures (see, e.g., Butler, supra), a potential difference of about 0.6 V usually exists between the anode and the cathode. Moreover, these electrodes are separated by only a few microns. Under these circumstances, silver ions concentrated within a thin enclosed electrolyte layer will experience a high field, possibly $10^4$–$10^5$ V m$^{-1}$. Consequently, positively charged silver ions will move toward the negatively polarized gold electrode. This process may well increase the rate of silver contamination above that arising from diffusion.

Furthermore, it has also been discovered that incidental silver contamination of gold can sometimes occur during the planar processing of these metals to form the microfabricated electrode structures used in the present invention. For this reason, it may be preferable to fabricate the WE and CRE on different wafers.

Before continuing, it should be pointed out that one of the perceived advantages of the Clark oxygen electrode and the Severinghaus carbon dioxide electrode (see, *J. Applied Physiology* (1958) 13:515) which are both enclosed structures, is that they operate equally well in both gases and liquids. With commercially available blood gas analyzers, this ability is an essential feature, because calibration is usually performed with wet gases supplied from cylinders. However, in the single-use cartridge devices disclosed in U.S. Pat. No. 5,096,669, the disclosure of which is incorporated in its entirety by reference herein, the use of an aqueous calibrant fluid rather than a wet gas was preferred. Of the different electrode structures disclosed herein it will be apparent that some are designed for calibration with a liquid whereas others can be calibrated with either a liquid or a wet gas.

The applicants have also surprisingly discovered, that open working electrode structures, such as those depicted in FIGS. 2A–2G, can be operated advantageously with a remote reference electrode that is either a "bare" silver-silver chloride or a layered device like that disclosed in U.S. Pat. No. 4,933,048 (Lauks), the disclosure of which is incorporated in its entirety by reference herein. As noted above, however, some embodiments require that the calibrant or sample provide a contiguous conductive segment (i.e., the conductive layer) between the two electrodes. This connection provides the low impedance path necessary to support the electrochemical processes occurring at the working electrode (WE) and the counter/reference electrode (CRE). Hence, in the present invention a "conductive layer" is any material that can provide such a low impedance path. Typically, the CL may be comprised of conducting polymers or other materials as described in U.S. Pat. No. 5,200,051. In a particular embodiment of the present invention, an EL also serves as the CL. Moreover, in a preferred embodiment, the CL may further comprise a dopant, such as halides, nitrates, phosphates, sulfates, and the like.

In a preferred embodiment of the present invention for measuring oxygen, the cathode is designated the WE, where the reduction of oxygen molecules takes place, and the anode is designated the CRE, where the oxidation of silver occurs.

Hence, according to the present invention, a sensing device is provided which can measure the oxygen concentration in a sample and which combines the advantages of a microfabricated electrode, including rapid wet-up from a dry-stored state, small current, predictable characteristics, and the like. At the same time, the present invention possesses desirable aspects of standard non-microfabricated devices, including signal stability resulting from minimal cross contamination between electrode components.

It is important to note that the present invention can be utilized in a wide variety of applications in addition to oxygen measurements. Indeed, the principles of the present invention may be applied to any planar microfabricated device in which silver contamination of another electrode surface may potentially occur. For example, it is applicable to a device in which carbon dioxide is measured with a quinhydrone couple at a gold electrode and the reference electrode is silver-silver chloride. See, for example, Van Kempen et al. *Respir. Physiol.* (1972) 14:366 and the discussions in the review by Hahn, C. E. W. *J. Phys. E: Sci. Instrum,* (1980) 13:470–482.

In addition, the present invention also addresses certain manufacturing issues related to a CRE fabricated as shown in FIG. 7B of U.S. Pat. No. 5,200,051 in which the geometry may adversely effect the reliability and reproducibility of the electrolyte and gas permeable layers when such layers are established using the microfabrication methods described therein. It is well known in the art that topographical features on silicon wafers can adversely affect the reproducibilities of the thickness uniformity of spun layers such as those described above.

Figure 2A:
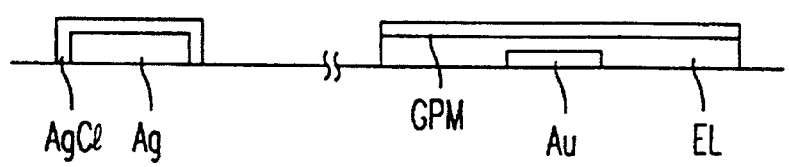
FIGS. 2A–2I illustrate various sensor configurations of the present invention. In certain cases, a conducting layer (CL), making electrical contact between the working electrode (WE) and the counter/reference electrode (CRE), is included in the sensor structure, which allows the sensing device to operate in a wet gas environment. In embodiments shown in FIGS. 2E and 2F, the electrolyte layer (EL) also functions as the CL. In embodiments shown in FIGS. 2G–2I, the EL can optionally be an aqueous electrolyte solution. It should be noted that the sensing device of the present invention can operate effectively whether the CRE is positioned proximal to WE or is located on a substrate separate from the substrate on which the WE is established. In addition, a bare CRE or one having an overlayered structure, such as the reference electrode (RE) disclosed in U.S. Pat. No. 4,933,048, can be utilized advantageously in the present invention. Note that CRE and RE are used interchangeably in the present application keeping in mind that a counter electrode is required with an amperometric but not a potentiometric measurement.

In particular, disparate geometries and sizes of underlying structures may unduly influence the contours of overlaid layers established by microfabrication techniques (e.g., spin-coating, sputtering, vapor deposition, and the like), thus changing the overall topography of the combined structures. For example, a pair of electrodes may be "subtantially different" in one dimension (that is, a difference of at least a factor of about two to about fifty), e.g., thickness. Thus a working electrode may be one-third (⅓) the thickness of a reference or counter electrode, as illustrated, e.g., in FIG. 2A, herein. If both structures were to be encompassed by an electrolyte, gas permeable or other overlaid layer, it is highly likely that the surface of the overlaid layer may set unevenly (i.e., may contain hills and valleys—the "adverse effects") due to the disparity in thickness of the underlying electrode structures. However, and again, as can be seen in FIG. 2A, separating the electrodes and establishing the EL and GPM layers (in an "open" fashion) provides a refinement in that one has greater control over the resulting thicknesses and geometries of the finished overall structures. At the same time, electrical contact between the electrode pair is maintained by the "open" structure.

Accordingly, the present invention is also directed to a method of establishing overlaid structures in a much more predictable, controlled fashion by separating the working electrode from the counter/reference electrode such that overlaid structures may be established only over one of the electrodes, particularly when the pair of electrodes are of substantially different sizes (in any or all three dimensions, especially thickness). The required distance separating the two electrodes may vary, of course, depending on the dimensions of the electrodes themselves. (For instance, a CRE can range from about 1 to about 5 µm in thickness, whereas WE can range from about 0.1 to about 0.5 µm in thickness.) However, one of ordinary skill in the art may readily determine the minimum required separation by systematically increasing the distance and observing the consequent effects on the topography of the overlaid layers. In the present case, this distance is approximately the same as the distance required to minimize cross contamination between the working and counter/reference electrodes. Standard equipment for profiling or determining thickness variations of layers on silicon substrates is suitable for making determinations of the type disclosed here. Such equipment will be familar to those skilled in the art of microfabrication.

Furthermore, the invention is not limited to just silver contamination of an adjacent electrode surface, but any chemical species arising at a counter or reference electrode which can cause an adverse or undesirable electrochemical property or effect on the working electrode. For example, the present invention eliminates mercury contamination arising from a calomel-type electrode, or other species, both metallic or organic, whose transport to the working electrode may be enhanced by the establishment of a gas permeable membrane.

Besides the advantages already noted, the present invention also allows a single reference electrode to be used, if desired, with a plurality of (i.e., more than one) working electrodes. In contrast, each working electrode of an enclosed structure requires its own reference electrode positioned underneath the gas permeable membrane. It should be understood that by "gas permeable membrane" or GPM, what is meant is a semipermeable membrane that has the property of excluding substantially all molecular species that cannot traverse the membrane in the gas phase. The membrane is permeable to typical gases, such as oxygen, nitrogen, and carbon dioxide. Such GPMs may comprise materials disclosed in U.S. Pat. No. 5,200,051 and U.S. Pat. No. 4,933,048. Preferably, the GPM is made from a silicone block copolymer. A more detailed description of the method of establishing the GPM can be found in the Examples, below, and in the disclosure of the above-mentioned patents.

Yet another advantage of the present invention over prior enclosed structures is that whereas only a finite amount of ions, e.g., chloride, is available in the enclosed structure to support the reference electrode reaction, the open structure allows the device to capture ions from beyond the immediate area of the electrode, e.g., from the surrounding medium, such as the calibrant fluid or the sample. It has been surprisingly discovered, also, that an open structure allows the WE and CRE components of the microfabricated device to be in closer proximity than may ordinarily be permissible in an enclosed structure. Though applicants do not wish to be limited by theory, it is believed that just as the open structure permits the device to "recruit" chloride ions from the surrounding media, the open structure also allows silver ions egress from the device to the media. The silver ions, in a closed structure, would ordinarily be more available or predisposed to contaminate an adjacent electrode.

Hence, as mentioned previously, the open structure of the present invention can be used with a standard exposed or bare silver-silver chloride reference electrode (See, e.g., FIG. 2A) or the reference electrode of U.S. Pat. No. 4,933,048 (See, e.g., FIG. 2B). An important feature of the open structure is that the architecture of the gas permeable membrane (GPM), including the materials used, its dimensions (e.g., surface area and thickness), and its positioning relative to the WE is such that the GPM still controls the flux of gases to the WE (in this case, the cathode) despite the fact that the GPM does not fully enclose the WE. Thus, in general, the overlap of the gas permeable membrane layer beyond the perimeter of the WE, itself, should be several times the radius of the WE. For example, with a 10 µm radius gold electrode it is preferred that the electrolyte layer is overlayed with a gas permeable layer that extends about 50 µm beyond the perimeter of the gold electrode. As a result, it has been observed by the present applicants that the gas flux from the "open" perimeter, passing through the plane of the electrolyte layer to the cathode, is negligible compared to the flux through the GPM, itself. It is well known that the flux of a molecule through any given material is a function of the molecule's solubility and diffusion coefficient and also the cross-sectional area and length of the material. Thus, a basic tenet may be that the path, which a dissolved gas might take from the open perimeter to the electrode surface, is kept long relative to the path traversed by the dissolved gas from the GPM to the electrode surface. For a 1 µm thick gelatin electrolyte layer, the 50 µm overlap is appropriate. Alternatively, the permeability of the photoformed gelatin film can be controlled by means of the ratio of crosslinker (e.g., dichromate) to gelatin solids in the mixture prior to deposition, as well as the duration and temperature of a bake step after exposure and development. Increased crosslinker, duration, and temperature of bake all contribute to a reduction in the permeability of the gelatin film to oxygen and other gases. Thus, the overlap of the electrolyte layer beyond the working electrode can be reduced accordingly, i.e., something less than 50 µm, depending on the degree of crosslinking effected by the amount of crosslinker present and/or the bake temperature and duration thereof. (See, for example, Brinker, C. J. and Scherer, G. W., in "Sol-Gel Science: The Physics and Chemistry of Sol-Gel Processing" Academic Press, 1990.)

Those skilled in the art will understand the method of calculating relative dimensions to ensure that the flux of oxygen through the plane of the electrolyte does not exceed a fixed percentage, e.g., 5%, 3%, 1%, or preferably 0.5% of that passing through the gas permeable membrane. The observed output characteristics are surprisingly similar to an enclosed structure and quite unlike the pin-hole electrode of U.S. Pat. No. 4,682,602 (Prohaska). Again, the microfabrication methods disclosed in U.S. Pat. No. 5,200,051 are especially advantageous in controlling the dimensions of the particular overlaid structures.

Figure 2B:
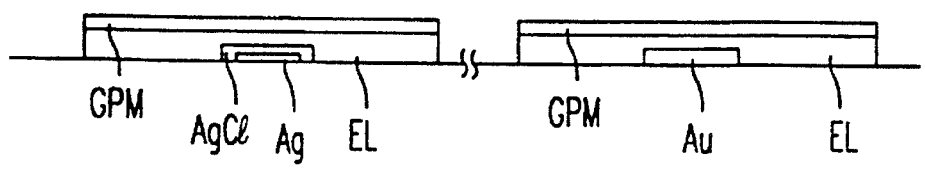

Suitable sensor structures fabricated on the same silicon chip are illustrated in FIGS. 2A and 2B. In the dimensions of the specific illustration, the horizontal distance between working electrode and the combined counter/reference electrode is greater than about 1 mm. Alternatively, but less conveniently, the CRE can be located on a separate chip.

When the open structure WE and reference electrodes are located on the same chip, the operational requirement for a conductive liquid being in position (i.e., in electrical contact) between them may be overcome by establishing a thin conductive layer (CL) in electrical communication with the two electrodes. The device with the established CL can now operate in a wet gas. The actual CL can take many forms. For example, a photoformed proteinaceous layer, e.g., dichromated gelatin, which is impregnated with salts and which can adsorb sufficient water to provide a conductive path, is one useful embodiment. A second viable embodiment, includes a conducting organic polymer which is stable in the presence of water and oxygen. Suitable conducting organic polymers may include, for example, polyaniline, polythiophene, polypyrrole and the like, which may optionally contain a dopant, e.g., iodide, boron trifluoride and the like.

Figure 2C:
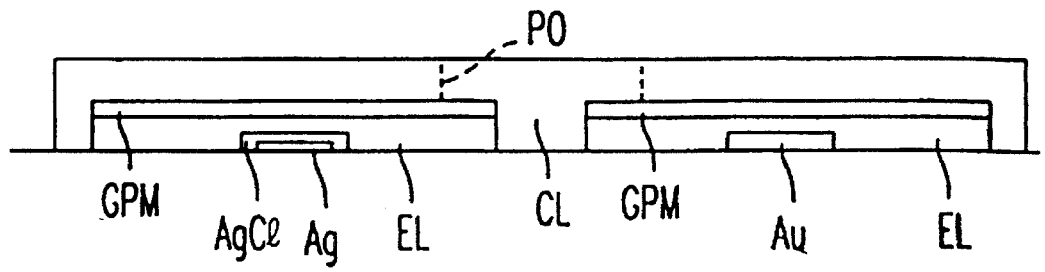
Figure 2D:
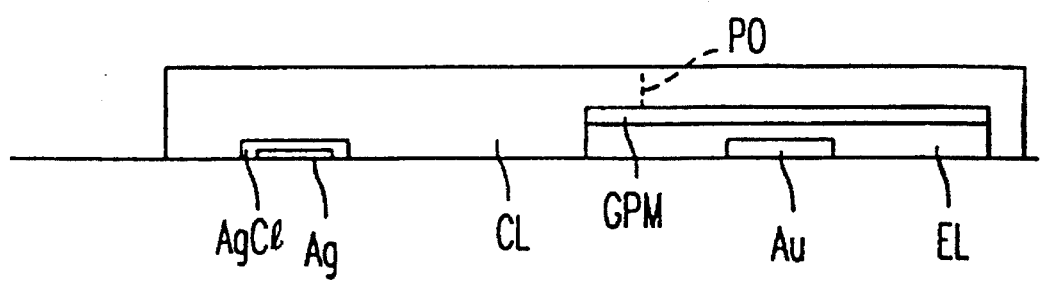
Figure 2E:
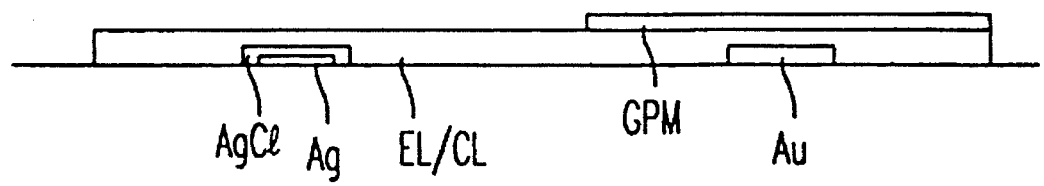
Figure 2F:
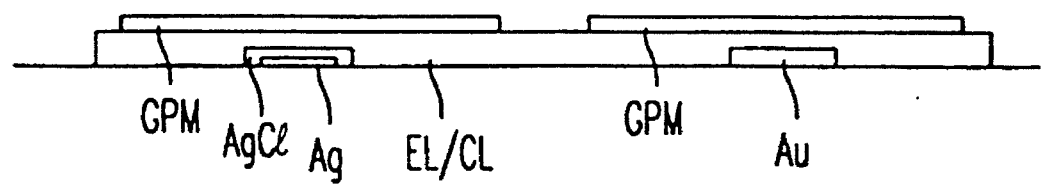

At FIGS. 2C and 2D, two embodiments are shown with a conductive layer established on the device. A partial or complete overlap is practical. Alternatively, the electrolyte layer may be extended to bridge the region between the electrodes of FIGS. 2A and 2B, as shown in FIGS. 2E and 2F.

Figure 2G:
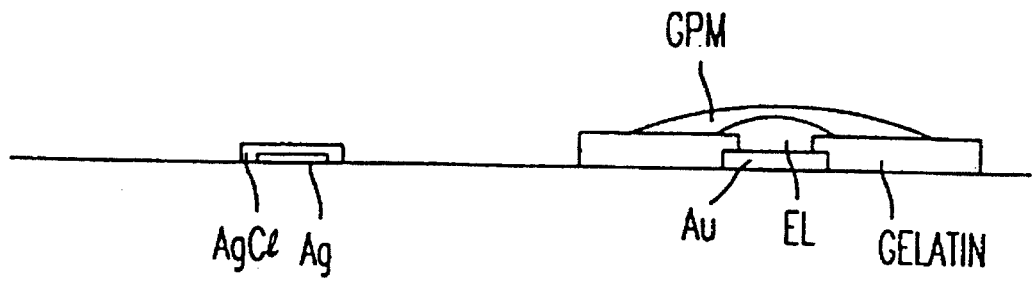
Figure 2H:
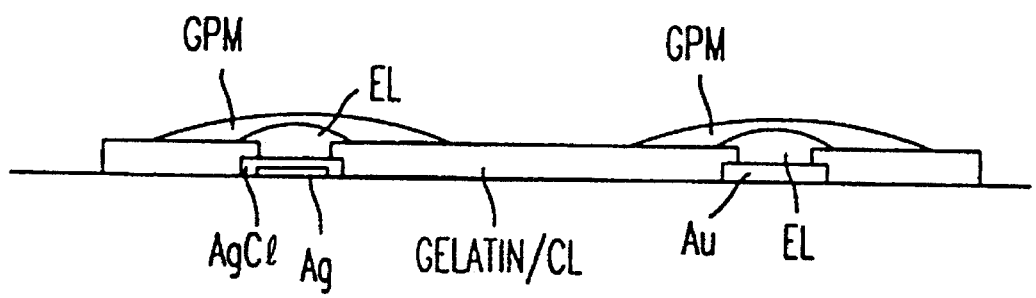
Figure 2I:
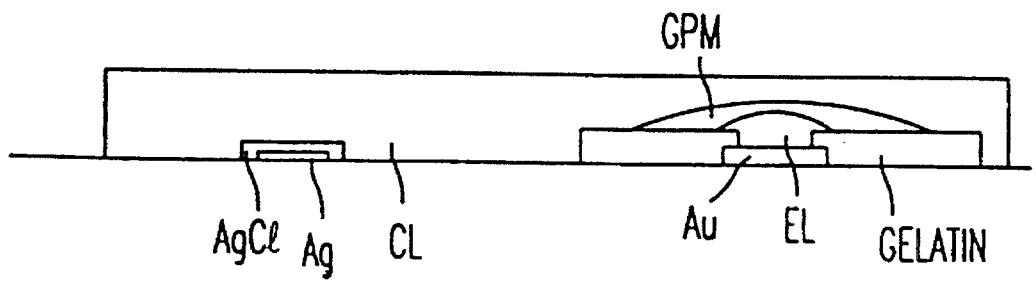

An important embodiment of the present invention addresses the problem of confining an EL in an open structure in which the EL may be comprised of a material that does not adhere to the surface of the chip or one that would dissolve if brought into direct contact with an aqueous medium. Functionality is based on the excellent adhesion of GPM materials such as silicone block copolymers, described in U.S. Pat. No. 5,200,051 to materials such as photoformable gelatins (a proteinaceous material) also described in this patent. Consequently, FIGS. 2G–2I show structures in which a proteinaceous layer, e.g., photoformed proteinaceous layer (PPL), is first established around the electrode before the EL, which is confined within the PPL, is established. The GPM is then established over the EL and at least a portion of the PPL. A suitable PPL comprising a photoformable fish gelatin containing a photoinitiator can be purchased from Norland Products, Inc., New Brunswick, N.J. Most preferably, the PPL is dichromated gelatin. Additional discussion of this and other materials suitable for this invention can be found in U.S. Pat. No. 5,200,051 (Cozzette), with specific details for PPLs in Section 6.1.3.

The above approach provides structural stability and integrity to the overall sensor configuration while allowing great flexibility in the range of components that may be chosen to make up the EL. Thus, even those EL compositions that one of ordinary skill in the art may associate only with non-microfabricated devices in which the GPM is held in place by an O-ring (and which EL compositions may contain soluble components, e.g., dissolved sugars or salts) may be accommodated by the open structures of the present invention.

Figure 2J:
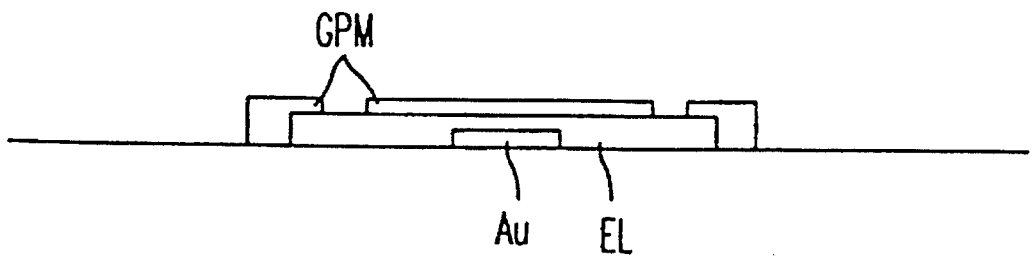
FIG. 2J illustrates a gold working electrode overlaid with successive layers of an electrolyte and a gas permeable membrane (GPM). The GPM is established so that the open perimeter is situated about the top surface of the sensor, as opposed to the sensor's extreme edges.

Finally, FIG. 2J illustrates yet another embodiment of the present invention in which the "open" perimeter of the sensing device is located on the upper surface. Thus, after the EL is established over the gold electrode, processing parameters can be altered to establish a GPM above the sensor and around the extreme edges of the EL, without completely enclosing the top surface of the EL. These methods will be evident from the disclosure on patterning siloxane-nonsiloxane copolymers in U.S. Pat. No. 5,200,051 which can be used to process the GPM described herein.

EXAMPLES

6.1. Oxygen Sensor

Figure 3A:
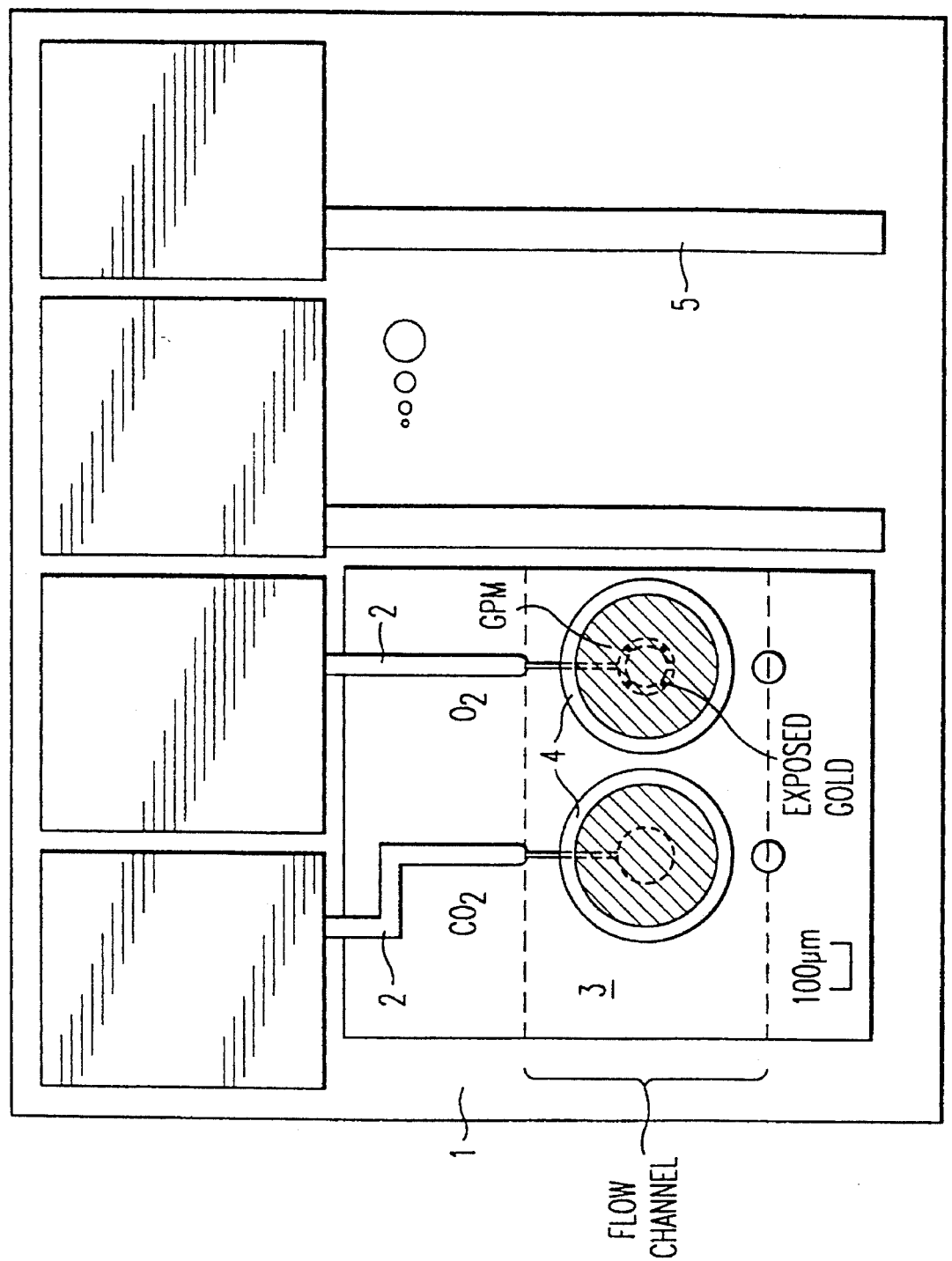
FIG. 3A shows a unit cell of a potentiometric $CO_2$ sensor and an amperometric oxygen sensor, which is adjacent to a counter/reference electrode, 5.
Figure 3B:
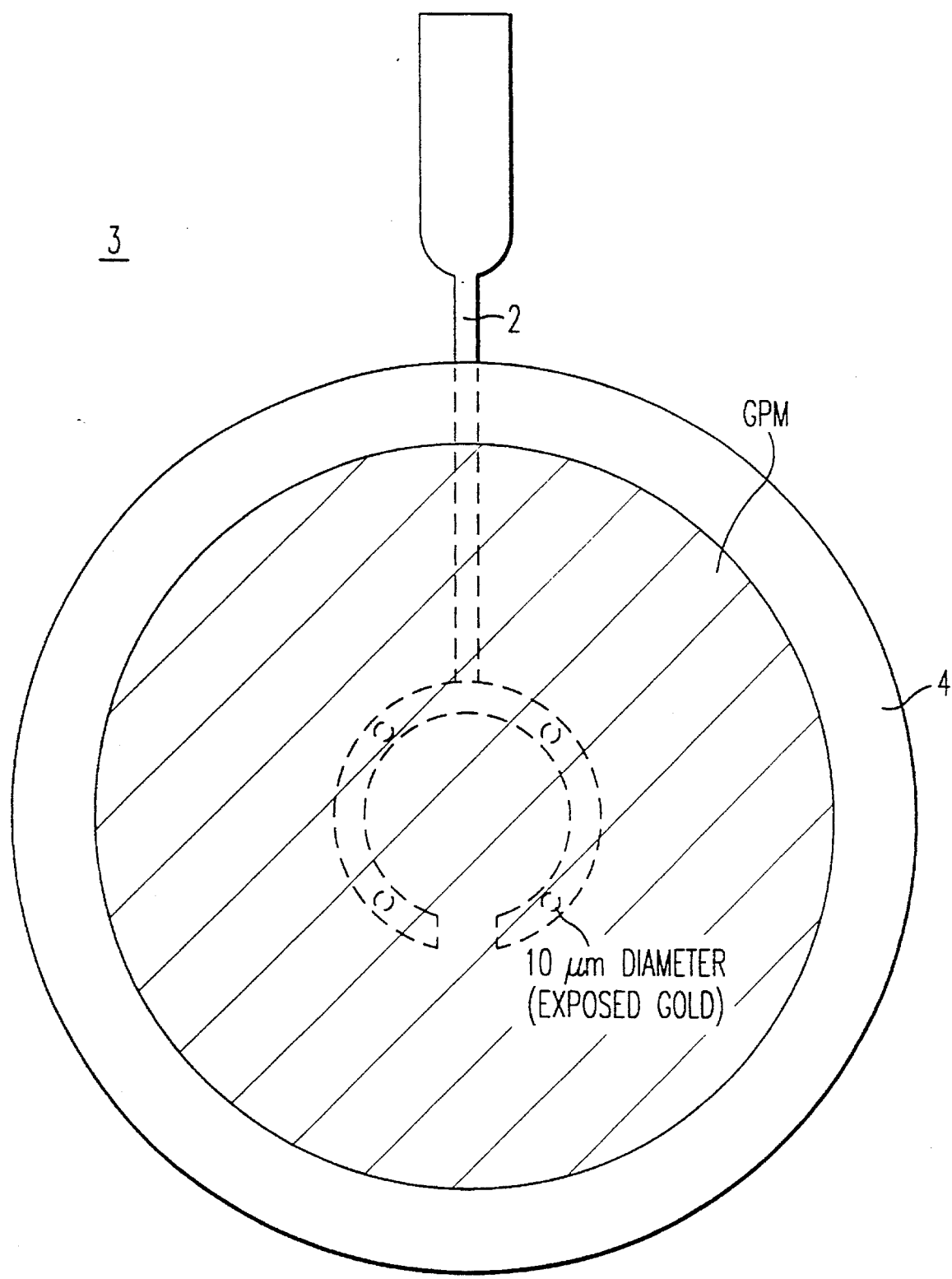
FIG. 3B illustrates an enlarged view of the $O_2$ sensor with 2, the gold electrode; 3, the polyimide layer (white); 4, the gelatin electrolyte layer; and GMP, gas permeable membrane.

A silicon wafer which has been thermally oxidized to produce a surface layer of silicon dioxide (1) is first sputtered with a layer of a titanium-tungsten alloy followed by a layer of gold (2). A standard photolithographic process is used to mask the metals for patterning to leave the unit cell structure shown in FIG. 3A. Polyimide (3, the white area) is spin-coated and then photoformed onto the wafer to passivate the conductive lines and define the exposed electrode surface area (four small circles on inner horse-shoe structure of 10 µm diameter each), as shown in FIG. 3A or 3B. A four-inch silicon wafer contains approximately three hundred unit cells.

A layer of dichromated fish gelatin is then spin-coated onto the wafer, exposed to ultraviolet radiation through a mask and then developed in water to leave the structure (4, thickness about 1 µm) shown in FIG. 3B. Wafers are then baked in an oven at 120° C. for one hour. Finally, a dimethylsiloxane-bisphenol A carbonate copolymer (GPM, large cross-hatched circle) of thickness 1 µm is established over the gelatin layer and patterned in a manner described in Section 6.1.5 of U.S. Pat. No. 5,200,051. FIG. 3A or 3B show the final oxygen electrode structure with dimensions that ensure substantial oxygen transport to the electrode through the GPM. Also, the dashed lines on FIG. 3A define the possible width of a liquid sample channel.

Post-processing of the sensor involves a soak step in an aqueous buffer solution (Borax-NaOH plus 50 mm NaCl is suitable.)

As stated previously the oxygen electrode can be operated with a bare silver-silver chloride electrode fabricated on the same (e.g., 5) or an adjacent silicone chip or with the reference electrode described in U.S. Pat. No. 4,933,048.

Using the above-described oxygen sensor, the concentration of oxygen in a blood sample is determined by first contacting the blood sample with the oxygen sensor. Next, a potential is applied to the working electrode relative to the counter/reference electrode effective to reduce molecules of oxygen at the working electrode. The current output of the device, a function of oxygen concentration, is then measured and related by a standard curve to the oxygen concentration in the sample.

6.2. Carbon Dioxide Sensor

Processing of metal and polyimide layers for a carbon dioxide sensor are the same as for the oxygen sensor described previously. Processing of the photoformable gelatin layer is similar except that, with use of a different mask, the region directly above the gold electrode is removed during development (See, e.g., FIG. 3A). An aqueous mixture of sodium bicarbonate quinhydrone, sodium chloride and sucrose is then dispensed onto the region directly over the gold electrode using the dispensing means described in, for example, Section 5.4 of U.S. Pat. No. 5,200,051.

A silicone layer may be established in the same manner as described previously for the oxygen sensor. Alternatively the gas permeable layer can be established by dispensing the membrane material. In this instance, polyvinyl chloride (PVC) dissolved in an organic solvent can be used as an alternative to the silicone.

By reference to a standard curve of potential versus carbon dioxide concentration, the $CO_2$ concentration in a blood sample is measured after the sample is contacted with the above-described $CO_2$ sensor. The potentiometric measurement relies on equilibria of dissolved carbon dioxide, which equilibrates to form hydrogen ions and bicarbonate ions. These ions, in turn, affect the quinhydrone potential as described previously by Van Kempen, above.

The same alternatives for a reference electrode described for the oxygen sensor are appropriate for the carbon dioxide sensor.

In a preferred embodiment, the sensors of the above-described Examples are housed in a disposable cartridge that is inserted into an external reading device, such as that described in U.S. Pat. No. 5,096,669 (Lauks), the disclosure of which is incorporated in its entirety by reference herein.

The foregoing examples are provided to serve as an illustration of the preferred embodiments of the present invention, which invention is not to be construed as being limited thereto as other embodiments of the present invention will be apparent to one of ordinary skill in the art after consideration of the objectives of the present invention in combination with the detailed descriptions provided herewith.

For example, the methods of determining gas concentration in an unknown fluid can be effected optionally by first calibrating the sensing device with a known sample. Further details on the advantageous use of such calibrating fluids during "wet up" of the device are found in the disclosure of U.S. Pat. No. 5,112,455, the entire disclosure of which is incorporated herein by reference.

What is claimed is:

1. A microfabricated sensing device for measuring a concentration of a dissolved gas in a liquid sample, comprising:

(a) a working electrode (WE) and a counter/reference electrode (CRE) established on the same or separate planar substrates, said WE and CRE being separated by a distance effective to minimize WE contamination by components of said CRE;

(b) an electrolyte layer (EL) established on said substrate and enclosing said WE; and (c) a gas permeable membrane (GPM) established on but not enclosing said EL and positioned over said WE, each of said GPM and EL having respective dimensions and configurations relative to said WE such that a flux of gas to said WE, from a liquid sample in contact with the device, is a function of an amount of gas passing through said GPM.

2. The device of claim 1 in which said distance is at least about 1 mm.

3. The device of claim 1 in which said WE comprises gold, said CRE comprises silver/silver chloride, said EL comprises a photoformed gelatin, and said GPM comprises a silicone block copolymer.

4. A microfabricated sensing device for measuring a concentration of a dissolved gas in a liquid sample, comprising:

(a) a planar substrate;

(b) a working electrode (WE) and a counter/reference electrode (CRE) established on said substrate and separated by a distance effective to minimize WE contamination by components of said CRE;

(c) an electrolyte layer (EL) established on said substrate and enclosing said WE; and (d) a gas permeable membrane (GPM) established on but not enclosing said EL and positioned over said WE, each of said GPM and EL having respective dimensions and configurations relative to said WE such that a flux of gas to said WE, from a liquid sample in contact with the device, is a function of an amount of gas passing through said GPM.

5. The device of claim 4 in which said distance is at least about 1 mm.

6. The device of claim 4 in which said WE comprises gold, said CRE comprises silver/silver chloride, said EL comprises a photoformed gelatin, and said GPM comprises a silicone block copolymer.

7. A method of measuring a concentration of a dissolved gas in a liquid sample, comprising the steps of:

(a) providing a microfabricated sensing device comprising (i) a working electrode (WE) and a counter/reference electrode (CRE) established on the same or separate planar substrates, said WE and CRE being separated by a distance effective to minimize WE contamination by components of said CRE, (ii) an electrolyte layer (EL) established on said substrate and enclosing said WE, and (iii) a gas permeable membrane (GPM) established on but not enclosing said EL and positioned over said WE, each of said GPM and EL having respective dimensions and configurations relative to said WE such that a flux of gas to said WE, from a liquid sample in contact with the device, is a function of an amount of gas passing through said GPM;

(b) contacting a liquid sample containing a gas to said device such that said liquid sample provides a low impedance path between said WE and CRE;

(c) applying a potential to said WE with respect to said CRE effective to allow molecules of the gas to undergo a redox reaction at said WE;

(d) measuring a current output of said device; and (e) determining a concentration of the gas based on said measured current.

8. The method of claim 7 in which said gas is oxygen.

9. A method of measuring a concentration of a dissolved gas in a liquid sample, comprising the steps of:

(a) providing a microfabricated sensing device comprising (i) a working electrode (WE) and a reference electrode RE established on the same or separate planar substrates, said WE and RE being separated by a distance effective to minimize WE contamination by components of said RE, (ii) an electrolyte layer (EL) established on said substrate and enclosing said WE, and (iii) a gas permeable membrane (GPM) established on but not enclosing said EL and positioned over said WE, each of said GPM and EL having respective dimensions and configurations relative to said WE such that a flux of gas to said WE, from a liquid sample in contact with the device, is a function of an amount of gas passing through said GPM;

(b) contacting a liquid sample containing a gas to said device such that said liquid sample provides a low impedance path between said WE and RE;

(c) measuring a potential between said WE and RE; and (d) relating said potential to a concentration of the gas in the liquid sample.

10. The method of claim 9 in which said gas is carbon dioxide.

11. A microfabricated sensing device for measuring a concentration of a gas in a sample, comprising:

(a) a working electrode (WE) and a counter/reference electrode (CRE) established on the same substrate, said WE and CRE being separated by a distance effective to minimize WE contamination by components of said CRE;

(b) an electrolyte layer (EL) established on said substrate and enclosing said WE;

(c) a conducting layer (CL) established on said substrate to provide electrical contact between said WE and said CRE; and (d) a gas permeable membrane (GPM) established on but not enclosing said EL and positioned over said WE, each of said GPM and EL having respective dimensions and configurations relative to said WE such that the flux of gas to said WE, from a sample in contact with the device, is a function of an amount of the gas passing through said GPM.

12. The device of claim 11 in which said EL is in electrical contact with said CRE, thus serving as said CL.

13. The device of claim 11 in which said sample is selected from the group consisting of air, a gas, wet air, a wet gas or liquid.

14. The device of claim 11 in which said distance is at least about 1 mm.

15. The device of claim 11 in which said WE comprises gold, said CRE comprises silver/silver chloride, said EL comprises a photoformed gelatin, and said GPM comprises a silicone block copolymer.

16. The device of claim 11 is which said EL comprises a photoformed gelatin whose permeability to gases has been reduced by an increased ratio of crosslinker to gelatin solids.

17. The device of claim 11 in which said EL comprises a photoformed gelatin whose permeability to gases has been reduced by an extended bake step at elevated temperature.

18. The device of claim 17 in which said photoformed gelatin had been baked at 120° C. for one hour.

19. The device of claim 11 in which said CL comprises a photoformed gelatin layer containing hygrocopic salts.

20. The device of claim 11 in which said CL comprises a conducting polymer.

21. The device of claim 20 in which said conducting polymer is selected from the group consisting of polypyrrole, polythiophene, and polyaniline.

22. The device of claim 21 in which said conducting polymer further comprises a dopant.

23. The device of claim 21 in which said conducting polymer further comprises a dopant selected from the group consisting of halides, nitrates, phosphates, and sulfates.

24. The device of claim 20 in which said conducting polymer further comprises a dopant selected from the group consisting of halides, nitrates, phosphates, and sulfates.

25. The device of claim 20 in which said conducting polymer further comprises a dopant.

26. A method of measuring a concentration of a gas in a sample, comprising the steps of:
(a) providing a microfabricated sensing device comprising (i) a working electrode (WE) and a counter/reference electrode (CRE) established on the same substrate, said WE and CRE being separated by a distance effective to minimize WE contamination by components of said CRE, (ii) an electrolyte layer (EL) established on said substrate and enclosing said WE, (iii) a conducting layer (CL) established on said substrate to provide electrical contact between said WE and said CRE, and (iv) a gas permeable membrane (GPM) established on but not enclosing said EL and positioned over said WE, each of said GPM and EL having respective dimensions and configurations relative to said WE such that a flux of gas to said WE, from a sample in contact with the device, is a function of an amount of gas passing through said GPM;
(b) contacting a sample containing a gas to said device;
(c) applying a potential to said WE with respect to said RE effective to allow molecules of the gas to undergo a redox reaction at said WE;
(d) measuring a current output of said device; and
(e) determining a concentration of the gas based on said current output.

27. The method of claim 26 in which the concentration of the gas is determined by comparing the measured current output to a standard curve relating current output to a partial pressure of a gas in a sample.

28. The method of claim 26 which further comprises contacting said microfabricated sensing device with a calibrating fluid before or after the device is contacted with a sample.

29. A method of measuring a concentration of a gas in a sample, comprising the steps of:
(a) providing a microfabricated sensing device comprising (i) a working electrode (WE) and a reference electrode (RE) established on the same substrate, said WE and RE being separated by a distance effective to minimize WE contamination by components of said RE, (ii) an electrolyte layer (EL) established on said substrate and enclosing said WE, (iii) a conducting layer (CL) established on said substrate to provide electrical contact between said WE and said RE, and (iv) a gas permeable membrane (GPM) established on but not enclosing said EL and positioned over said WE, each of said GPM and EL having respective dimensions and configurations relative to said WE such that a flux of gas to said WE, from a sample in contact with the device, is a function of an amount of gas passing through said GPM;
(b) contacting a sample containing a gas to said device;
(c) measuring a potential between said WE and RE; and
(d) determining a concentration of the gas based on said measured potential.

30. The method of claim 29 in which the concentration of the gas is determined by comparing the measured potential to a standard curve relating potential to a partial pressure of a gas in a sample.

31. The method of claim 29 which further comprises contacting said microfabricated sensing device with a calibrating fluid before or after the device is contacted with a sample.

32. A microfabricated sensing device for measuring a concentration of an analyte in a liquid sample, comprising:
(a) a working electrode (WE) and a counter/reference electrode (CRE) established on the same planar substrate, said WE and CRE being substantially different in at least one dimension;
(b) at least a first layer established over said WE, said WE and CRE being separated by a distance effective to minimize adverse effects of said substantially different at least one dimension on topological features of said first layer.

33. The device of claim 32 in which said analyte is a dissolved gas.

34. The device of claim 32 in which said first layer comprises an electrolyte layer.

35. The device of claim 34, further comprising a second layer established over said first layer.

36. The device of claim 35 in which said second layer comprises a gas permeable layer positioned over said WE but which does not enclose said first layer.

37. The device of claim 32 in which said dimension is the thickness of said electrodes.

38. The device of claim 32 in which said distance is at least about 1 mm.

* * * * *

UNITED STATES PATENT AND TRADEMARK OFFICE
CERTIFICATE OF CORRECTION

PATENT NO. : 5,514,253
DATED : May 7, 1996
INVENTOR(S) : DAVIS, Graham

It is certified that error appears in the above-identified patent and that said Letters Patent is hereby corrected as shown below:

Column 5, line 18. Delete "solid" and insert therefore --dashed--.

Column 5, line 18. Delete "dashed" and insert therefore --solid--.

Column 5, line 52. Delete "GMP" and insert therefore --GPM--.

Column 11, line 56. Delete "mm" and insert therefore --mM--.

Signed and Sealed this

Twenty-seventh Day of March, 2001

Attest:

NICHOLAS P. GODICI

Attesting Officer  Acting Director of the United States Patent and Trademark Office